(12) United States Patent
Lin et al.

(10) Patent No.: US 8,420,394 B2
(45) Date of Patent: Apr. 16, 2013

(54) CULTURING ECTODERMAL CELLS UNDER REDUCED OXYGEN TENSION

(76) Inventors: Chih-Min Lin, San Diego, CA (US); Alex Wharazi, San Diego, CA (US)

(*) Notice: Subject to any disclaimer, the term of this patent is extended or adjusted under 35 U.S.C. 154(b) by 647 days.

(21) Appl. No.: 12/410,406

(22) Filed: Mar. 24, 2009

(65) Prior Publication Data

US 2010/0055757 A1 Mar. 4, 2010

Related U.S. Application Data

(60) Provisional application No. 61/093,238, filed on Aug. 29, 2008.

(51) Int. Cl.
*C12N 15/02* (2006.01)

(52) U.S. Cl.
USPC .......................... 435/384; 435/387; 435/392

(58) Field of Classification Search ................. None
See application file for complete search history.

(56) References Cited

U.S. PATENT DOCUMENTS

| | | |
|---|---|---|
| 6,610,540 B1 | 8/2003 | Csete et al. |
| 6,759,242 B1 | 7/2004 | Csete et al. |
| 6,846,641 B2 | 1/2005 | Wieloch et al. |
| 7,303,912 B2 | 12/2007 | Wahlberg et al. |

OTHER PUBLICATIONS

Lister et al. The Generation of Dopaminergic Neurons by Human Neural Stem Cells Is Enhanced by Bcl-XL, Both In Vitro and In Vivo. Journal of Neuroscience, 2004, vol. 24, pp. 10786-10795.*

Villa et al. Establishment and Properties of a Growth Factor-Dependent, Perpetual Neural Stem Cell Line from the Human CNS. Experimental Neurology, 2000, vol. 161, pp. 67-84.*

Zhang et al. Characteristics of Neural Stem Cells Expanded in Lowered Oxygen and the Potential Role of Hypoxia-Inducible Factor-1Alpha. Neuro-Signals, Jul. 2006, vol. 15, pp. 259-265.*

Jurga et al Neurogenic Potential of Human Umbilical Cord Blood: Neural-Like Stem Cells Depend on Previous Long-Term Culture Conditions.. J. Neuroscience Res., 2006, vol. 83, pp. 627-637.*

Carpenter et al. In Vitro Expansion of a Multipotent Population of Human Neural Progenitor Cells..Experimental Neurol., 1999, vol. 158, 265-278.*

Nijnik, et al.; DNA repair is limiting for haematopoitic stem cells during ageing.; Nature; Jun. 2007; vol. 447-7; 686-691; Nature Piblishing Group; USA.

Roitbak T., et al.; J Cereb Blook Flow Metab.; Sep. 2008; 1530-1542; vol. 28-9; Epub.; USA.

Zhang, CP., et al.; Neurosignals.; 2006-2007; 259-265; vol. 15-5; Epub.; USA.

Zhao T., et al.; Shen Li Xue Bao; Jun. 25, 2007; 273-277; vol. 59-3; Pubmed.; USA.

Zhull., et al.; Mol Neurobiol; 2005; 231-242; vol. 31-(1-3); Pubmed.; USA.

* cited by examiner

*Primary Examiner* — Deborah Crouch
(74) *Attorney, Agent, or Firm* — Timothy M. Brown, Esq.

(57) ABSTRACT

Disclosed are methods for expanding stem cells that use a unique combination of environmental factors and cell culture conditions to produce stem cells having enhanced proliferation and differentiation characteristics. Also disclosed are methods for enhancing the engraftment and/or migratory potential of stem cells for therapeutic uses. Stem cells having unique proliferation, differentiation, migratory and engraftment characteristics are also disclosed.

13 Claims, 7 Drawing Sheets

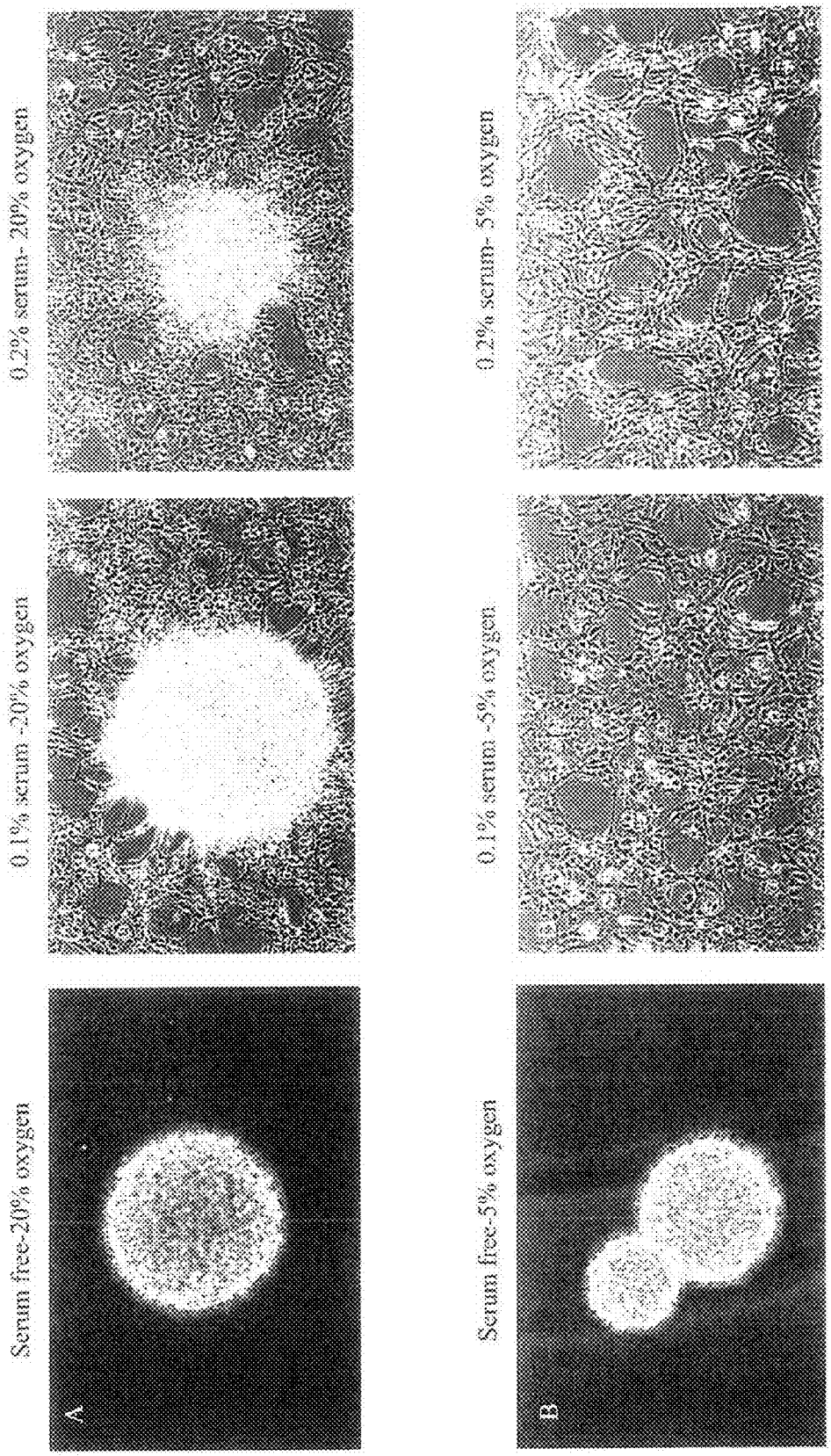

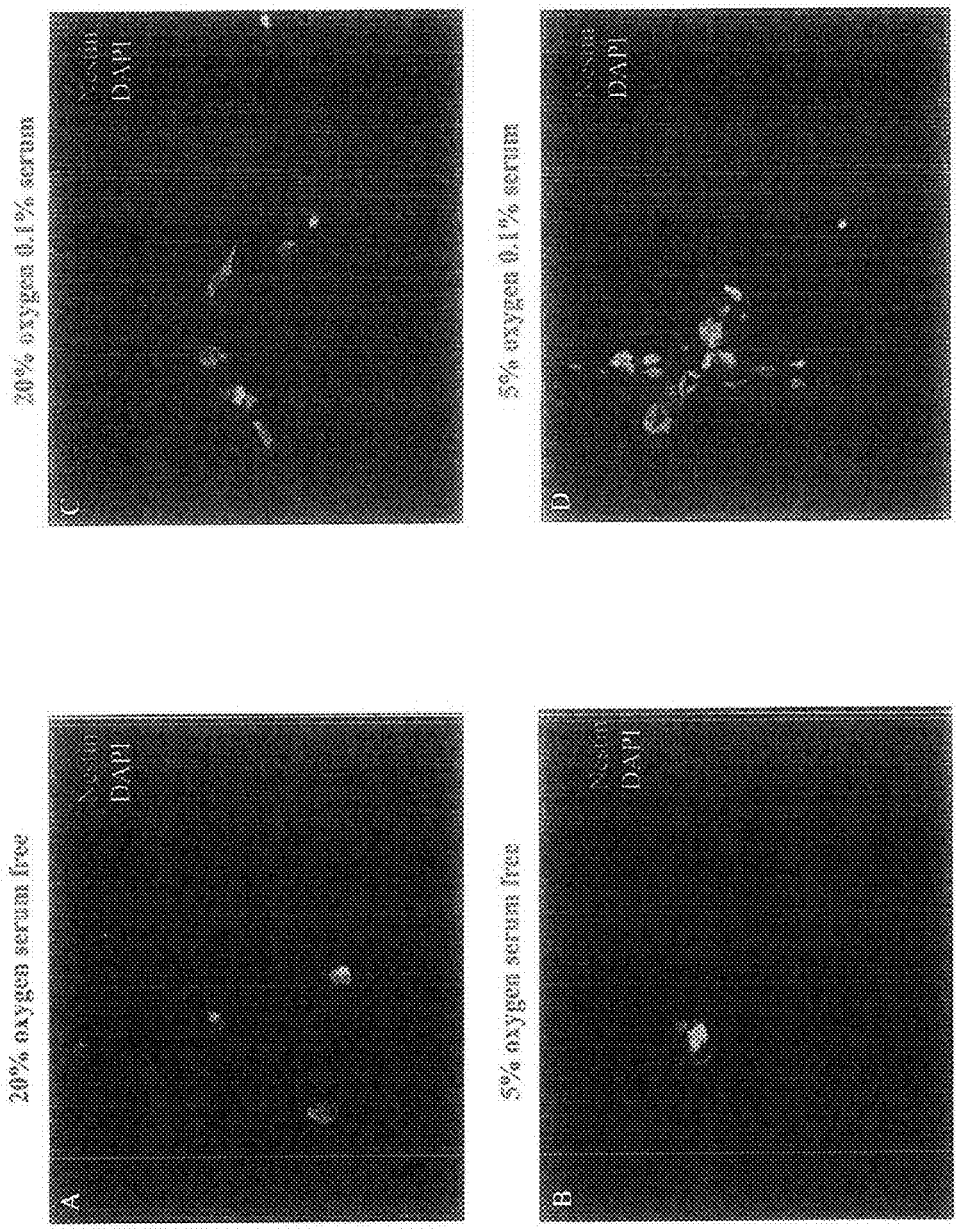
Figure 2. Progenitor marker, nestim expression in different culture condition cells

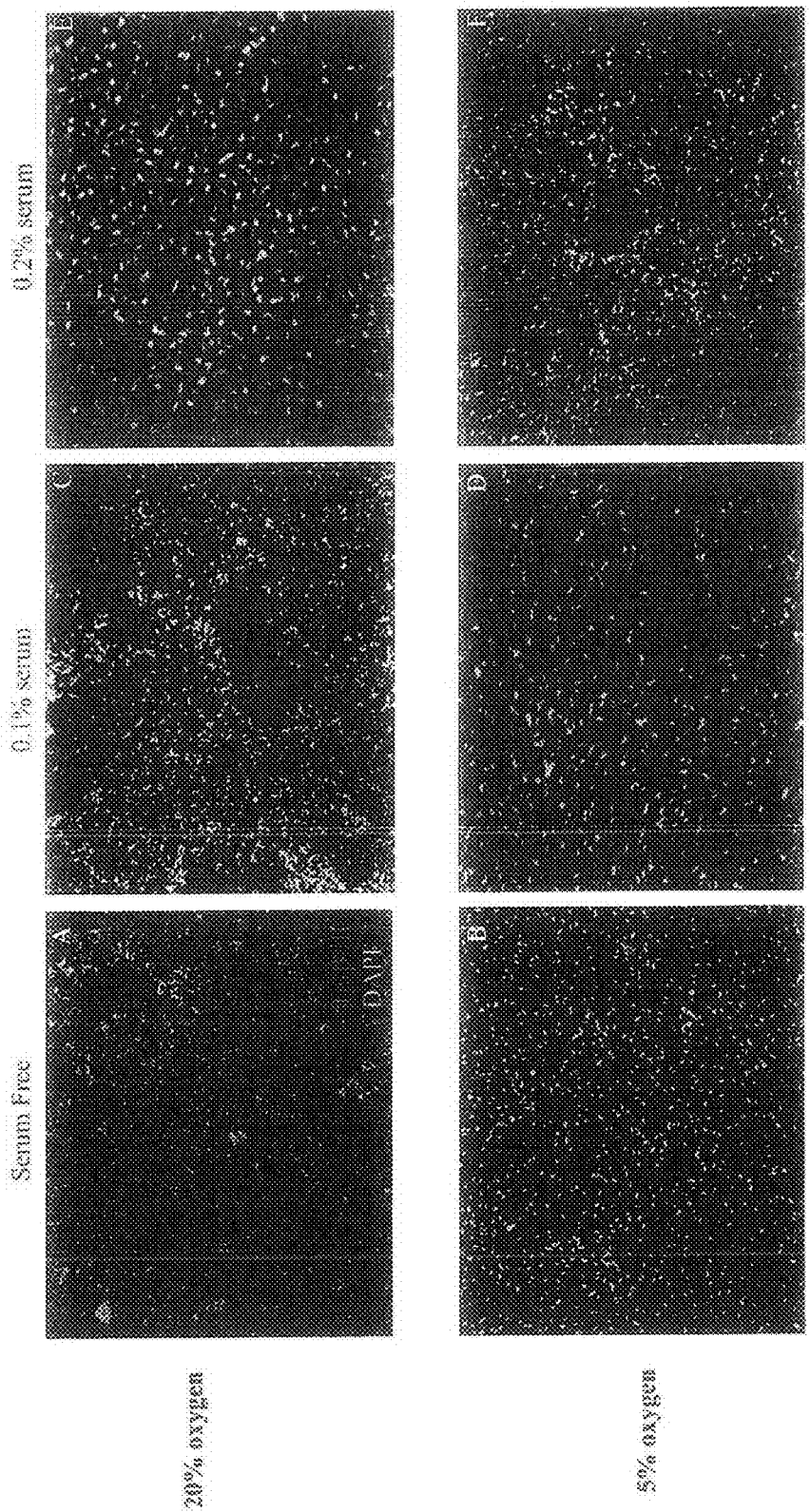

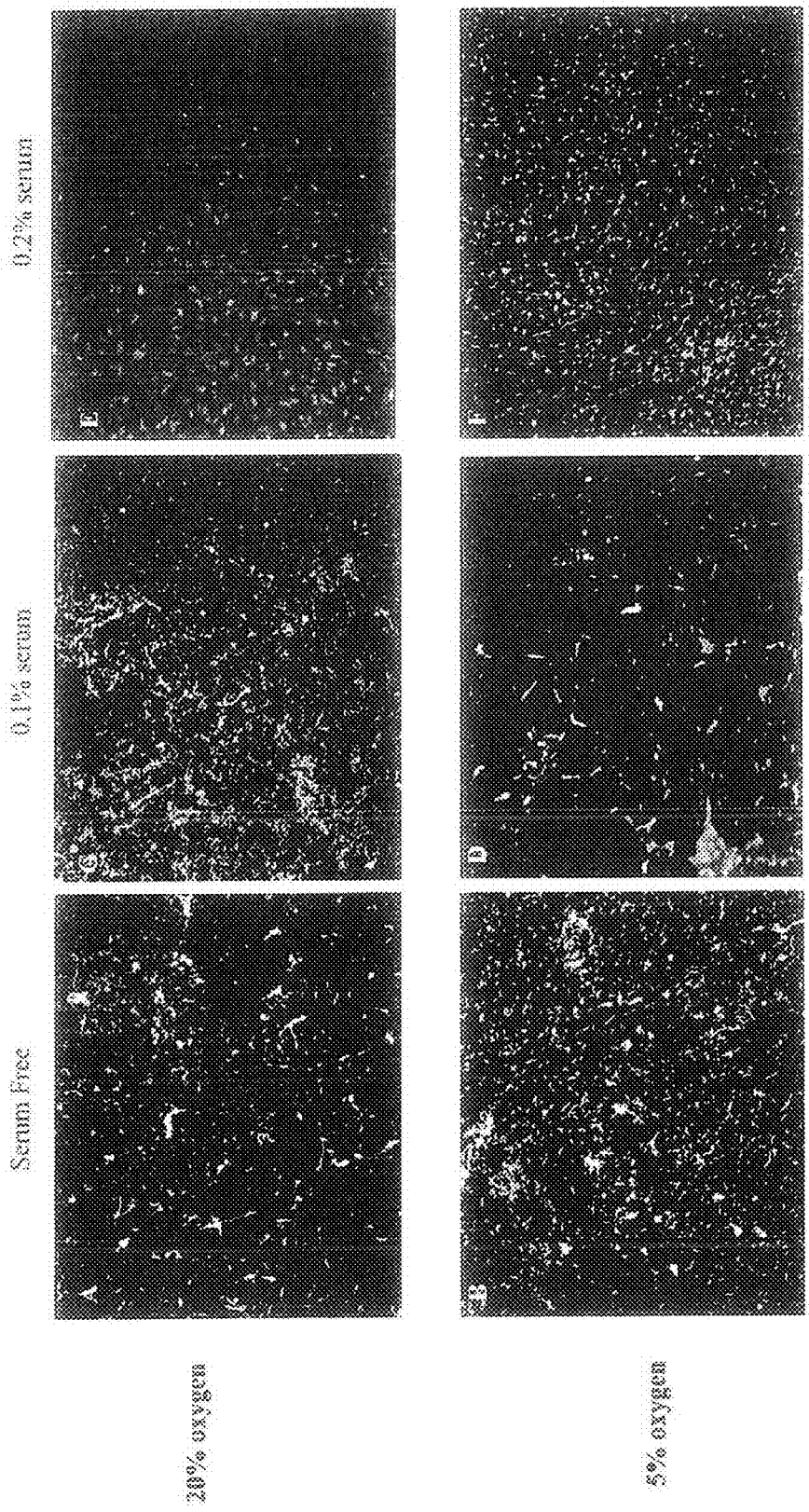

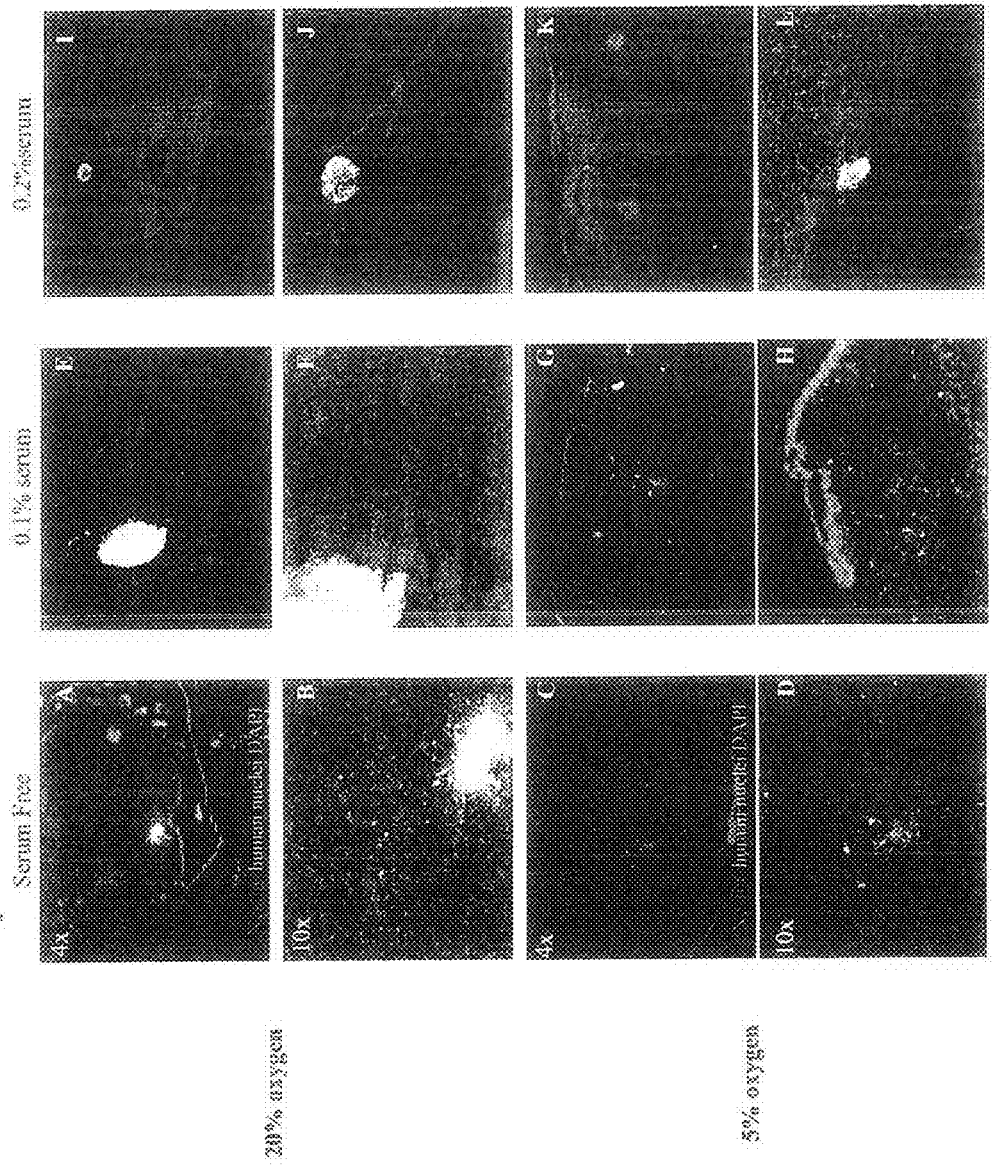

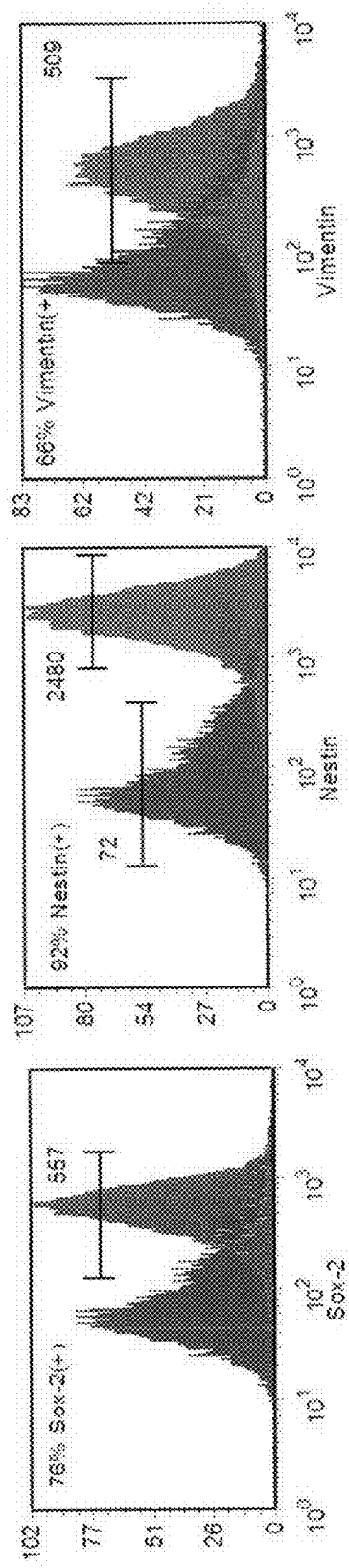
Figure 6. Neural progenitor marker expressions in 0.1% serum and 5% oxygen conditioned cells

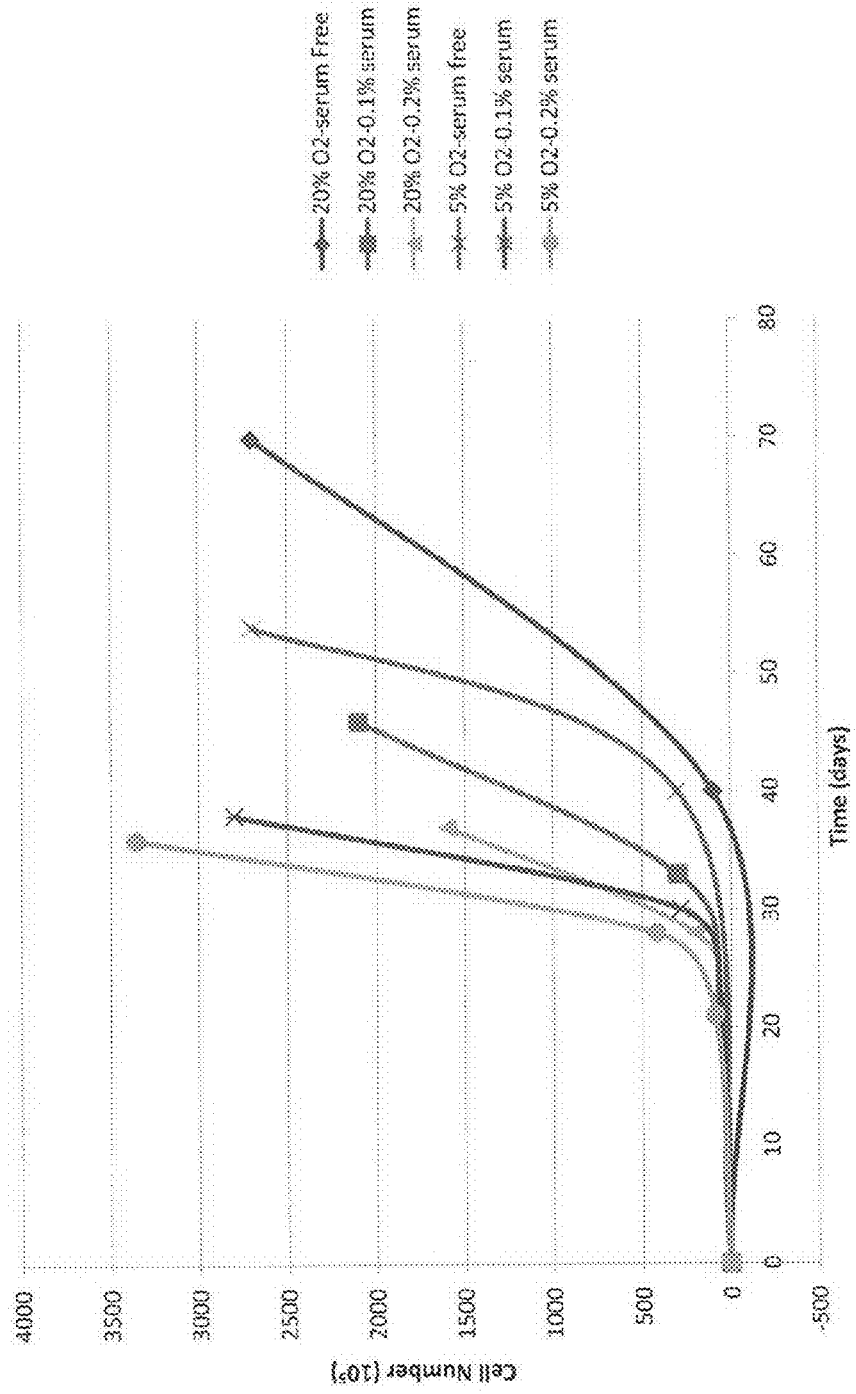

CULTURING ECTODERMAL CELLS UNDER REDUCED OXYGEN TENSION

This application claims priority to provisional application Ser. No. 61/093,238 filed on Aug. 29, 2008, the entire contents of which are incorporated herein by reference.

FIELD OF THE INVENTION

The invention relates to cells and stem cell culture. More particularly, the invention relates to a method of cell culture that uses a unique combination of environmental factors and culture conditions to produce a novel stem cell line having enhanced proliferation and differentiation characteristics.

BACKGROUND

Stem cells have shown great promise in treating a wide range of medical conditions. However, stem cell therapy often requires the administration of very large numbers of stem cells which are produced by the in vitro) expansion of tissue explants. Because stem cells are present in tissues in relatively small numbers, it is difficult to generate large numbers of stem cells for therapeutic use. This problem is complicated by the loss of differentiation potential that characterizes in vitro stem cell culture. As stem cells spend more time in culture and are encouraged to undergo multiple cell divisions, the differentiation potential of the stem cells diminishes (BMC Cell Biol. 2008 Oct. 28; 9:60; J Cell Physiol. 2005 November; 205(2):194-201). Thus, stem cells must be harvested after only a limited number of cell divisions in order to obtain stein cells having a desired level of differentiation potential.

What is needed in the art therefore is a method for expanding stem cells that extends the length of time that stem cells can remain in culture, permits the cells to undergo a greater number of divisions, and allows the stem cells to retain a desired level of stem cell differentiation and therapeutic potential.

SUMMARY OF INVENTION

The invention uses environmental factors and cell nutrient conditions to dramatically improve the speed and yield of stem cell manufacture. The invention accomplishes this by increasing cell proliferation and inhibiting the degradation of stem cell potential that characterizes the in vitro expansion of stem cells. Inhibiting the loss of differential potential increases stem cell yield by allowing the stem cells to undergo a greater number of passages while retaining a desired level of potency. The invention accomplishes this while providing the unexpected result of producing a population of stem cells having unique characteristics.

One objective of the invention is to enhance the differentiation potential of an in vitro population of stem cells comprising providing a population of stem cells, culturing the population of stem cells under conditions suitable to expand the population of stem cells, and exposing the population of stem cells to at least one environmental factor, wherein the environmental factor(s) enhances the differentiation potential of the stem cell population relative to a control stem cell population that is not exposed to the environmental factor(s).

A further objective of the invention is to provide stem cells, including neural stem cells, that have a unique biological activity comprising providing stem cells, culturing the stem cells under culture conditions suitable to expand the population of stem cells, and exposing the stem cells to at least one environmental factor, wherein the at least one environmental factor confers upon the stem cells a unique biological activity.

A further objective of the invention is to provide a method for culturing a population of stem cells comprising providing a population of stem cells, culturing the population of stem cells under conditions suitable to expand the population of stem cells, and exposing the stem cells to at least one environmental factor, wherein the environmental factor enhances the proliferation and/or differentiation potential of the stem cell population relative to a control stem cell population that is not exposed to the environmental factor(s).

A further objective of the invention is to provide a method for enhancing the differentiation potential of a population of neural stem cells comprising providing a population of neural stem cells, culturing the population of neural stem cells under conditions suitable to expand the population of neural stem cells, and exposing the population of neural stem cells to at least one environmental factor, wherein the environmental factor enhances the differentiation potential of the population of neural stem cells relative to a control neural stem cell population.

A further objective of the invention is to provide a method for culturing neural stem cells comprising providing neural stem cells, placing the neural stem cells in contact with culture medium comprising serum, and culturing the neural stem cells under culture conditions comprising reduced oxygen tension, wherein the reduced oxygen tension enhances the differentiation potential of the neural stem cells.

A further objective of the invention is to provide an in vitro cell culture comprising stem cells and culture medium comprising serum, wherein the culture medium has an oxygen tension that is less than about 5%, and wherein the stem cells are selected from the group consisting of mesenchymal stem cells, ectodermal stem cells and endodermal stem cells.

A further objective of the invention is to provide an in vitro cell culture comprising neural stem cells and culture medium comprising serum, wherein the culture medium has an oxygen tension level that is less than atmospheric oxygen.

A further objective of the invention is to provide a method for increasing the migratory and engraftment potential of a stem cell comprising providing a stem cell, culturing the stem cell under suitable cell culture conditions, and exposing the stem cell to at least one environmental factor, wherein exposing the stem cell to the environmental factor(s) increases the migratory and engraftment potential of the stem cell relative to a control stem cell that has not been exposed to the environmental factor(s).

A further objective of the invention is to provide neural stem cells for use in regenerative cell therapy comprising providing neural stem cells, culturing the neural stem cells under conditions suitable to expand the neural stem cells, and exposing the neural stem cells to an environmental factor that enhances the biological activity of the stem cell relative to control neural stem cells which are not exposed to the environmental factor.

BRIEF DESCRIPTION OF THE DRAWINGS

FIG. 1. Cell morphologies of neural progenitors under various culture conditions. Neural stem cells were collected from the same human fetal brain of eight weeks human embryo. Neural stem cells were divided into six groups. Neural stem cells form neurospheres when they were cultured in serm free conditions. However, neural progenitors become adherent when medium containing serum. A showed the cell morphology in serum free culture medium under 20% oxygen and 5% $CO_2$ culture condition. B showed the cell morphology in serum free culture medium under 5% oxygen and 5% $CO_2$ culture condition. C showed the cell morphology in 0.1% serum culture medium under 20% oxygen and 5% $CO_2$ culture condition. D showed the cell morphology in 0.1% serum culture medium under 5% oxygen and 5% $CO_2$ culture condition. E showed the cell morphology in 0.2% serum culture medium under 20% oxygen and 5% $CO_2$ culture condition. F showed the cell morphology in 0.2% serum culture medium under 5% oxygen and 5% $CO_2$ culture conditions.

FIG. 2 Progenitor marker, nestin expression in different culture conditions. Neural precursor marker, nestin was expressed in all different culture conditioned cells at passage 4. A showed the nestin expression pattern in serum free 20% oxygen conditioned cells. B showed the nestin expression pattern in serum free 5% oxygen conditioned cells. C showed the nestin expression pattern in 0.1% serum 20% oxygen conditioned cells. D showed the nestin expression pattern in serum free 5% oxygen conditioned Adsf.

FIG. 3. Tubulin-β (Tu-β III) expression in different culture conditioned cells after in vitro differentiation. All conditioned cells were collected and seeded in laminin coated cover slip under no mitogens, 10% serum, and 20% oxygen culture condition for two weeks. Neuron marker, Tu-β III was used for detecting neurons after differentiation. A showed Tu-β III expression pattern under serum free and 20% oxygen condition. B showed Tu-β III expression pattern under serum free and 5% oxygen condition. C showed Tu-β III expression pattern under 0.1% serum and 20% oxygen condition. D showed Tu-β III expression pattern under 0.1% serum and 5% oxygen condition. E showed Tu-β III expression pattern under 0.2% serum and 20% oxygen condition. F showed Tu-β III expression pattern under 0.2% serum and 5% oxygen condition. 0.2% serum under 20% oxygen showed no Tu-βIII expression. However, Tu-βIII expression was expressed in 0.2% serum under 5% oxygen which suggests oxygen tension rescue cells along neural lineage.

FIG. 4. Glial fibrillary acidic protein (GFAP) expression in different culture conditioned cells after in vitro differentiation. All conditioned cells were collected and seeded in laminin coated cover slip under no mitogens, 10% serum, and 20% oxygen culture condition for two weeks. Neuron marker, GFAP was used for detecting neurons after differentiation. A showed GFAP expression pattern under serum free and 20% oxygen condition. B showed GFAP expression pattern under serum free and 5% oxygen condition. C showed GFAP expression pattern under 0.1% serum and 20% oxygen condition. D showed GFAP expression pattern under 0.1% serum and 5% oxygen condition. E showed GFAP expression pattern under 0.2% serum and 20% oxygen condition. F showed GFAP expression pattern under 0.2% serum and 5% oxygen condition. 0.2% serum under 20% oxygen showed no GFAP expression. However, GFAP expression was expressed in 0.2% serum under 5% oxygen which suggests oxygen tension rescue cells along neural lineage.

FIG. 5. In vivo potency test: different cell migration activities showed in chicken embryonic brain. All conditioned cells were collected for transplantation in chicken embryonic brain for potency assay. $2 \times 10^5$ cells were microinjected into the ventricle of forebrain. Brains were collected after 6 days transplantation for immunohistochemistry. Human specific nuclei and nestin antibodies were used for tracing cell migration after in injection in host brain. A and B showed serum free and 20% oxygen cultured cells migrate and incorporate into host brain from ventricle through ventricular zone into striatum. C and D showed serum free and 20% oxygen cultured cells migrate into host brain from ventricle through ventricular zone into striatum. E and F showed 0.1% serum and 20% oxygen cultured cells aggregate between ventricle and ventricular zone and some cells migrate into host brain from ventricle through ventricular zone into striatum. G and H showed 0.1% serum and 5% oxygen cultured cells migrate into host brain. I and J showed 0.2% serum and 20% oxygen cultured cells aggregate in ventricle and no detection of migration. K and L showed 0.2% serum and 5% oxygen cultured cells aggregate between ventricle and some cells migrate into ventricular zone of brain.

FIG. 6. Neural progenitor marker expressions in 0.1% serum and 5% oxygen conditioned cells. Sox 2, nestin and Vimentin were used as progenitor markers for 0.1% serum and 5% oxygen conditioned cells on passage 4.

FIG. 7. Oxygen tension and serum conditional medium increase cell proliferation. NSCs were cultured in 6 different culture conditions. The growth rate showed that 5% oxygen tension increases cell proliferation as well as in serum conditional medium.

DEFINITIONS

The term "stem cell" refers to an undifferentiated cell which has the ability to both self-renew (through mitotic cell division) and undergo differentiation to form a more specialized cell. Stem cells have varying degrees of potency. A precursor cell is but one example of a stem cell.

The term "precursor cell" "tissue precursor cell," or "progenitor cell" refers to an undifferentiated cell that is committed a specific developmental pathway. Precursor cells have limited proliferative ability. "A neural precursor," is one example of a precursor cell that is dedicated to the development of a neuron, glial cell or astrocyte. Another non-limiting example of a progenitor cell is a neuronal progenitor cell which has the ability to differentiate to become a neuronal cell.

The term "neural stem cell" refers to an ectodermal stem cell having the ability to self-renew and differentiate to form a plurality of neural cell phenotypes. As used herein, "neural cell" refers to cells belonging to the neural cell lineage, including neuronal cells (i.e. unipolar, bipolar and multipolar neurons) and glial cells (i.e. oligodendrocytes, Schwann cells, astrocyles, and microglia). "Neural-potent," or "neural-potency," refers to the ability of a stem cell to assume a neural cell phenotype.

"Differentiation" refers to the biological process by which a less specialized cell becomes a more specialized cell type. For example, during embryonic development, pluripotent embryonic stem cells "differentiate" to form multipotent mesenchymal, ectodermal and endodermal stem cells, each of which are limited to a specific developmental pathway (i.e. range of tissues).

"Differentiation potential," "cell potential," "plasticity" and "potential" are used interchangeably herein to refer to the ability of a stem cell to differentiate into one or more specialized cell types.

"Pluripotent" or "pluripotency," refers to a stem cell having the potential to form specialized cells belonging to the mesoderm, endoderm and ectoderm tissue lineages.

The term "multipotent," or "multipotency" refers to the ability of a stem cell to form more than one cell type belonging to a single germ lineage (e.g. the endoderm or ectoderm or mesoderm). For example, a cell which has the ability to form chondrocytes, adipocytes and osteocytes is a multipotent mesenchymal cell.

"Unipotent," or "unipotency," refers to the ability of a progenitor cell to form a specific, terminal cell type. For example, a neuronal progenitor cell is unipotent for the formation of a neuron.

"Mesenchymal cells," are mesodermal germ lineage cells which may or may not be differentiated. The mesenchymal cells of the invention include cells at all stages of differentiation beginning with multipotent mesenchymal stem cells, down to fully differentiated terminal cells.

"Ectodermal cells," are ectodermal germ lineage cells which may or may not be differentiated. The ectodermal cells of the invention include cells at all stages of differentiation beginning with multipotent ectodermal stem cells, down to fully differentiated terminal cells.

"Endodermal cells," are endodermal germ lineage cells which may or may not be differentiated. The endodermal cells of the invention include cells at all stages of differentiation beginning with multipotent endodermal stem cells, down to fully differentiated terminal cells.

As used herein, the term "environmental factor" means an agent, condition, or form of energy that when exposed to a stem cell, enhances the stem cell's proliferation, differentiation potential, in vivo engraftment ability, and/or in vivo migratory ability relative to a control stem cell that is not exposed to such agent, condition, or form of energy. Environmental factors include, but are not limited to, reduced oxygen tension, electromagnetic energy, mechanical energy, metabolic deprivation, barometric variation, exposure to a chemical agent, and combinations thereof.

"Proliferation" refers to an increase in the number of cells in a population by means of mitotic cell division. "Increased proliferation," or "enhanced proliferation" refers to a measurable increase in the proliferation of a stem cell's in response to exposure to an environmental factor(s), relative the proliferation of a control stem cell that is not exposed to such environmental factor(s).

"Retaining stem cell potency," "maintaining stem cell potency," "enhancing differentiation potential," "inhibiting the loss of stem cell differentiation potential," and the like, refer to the ability of an environmental factor(s) to increase, or reduce the loss of, a stem cell's plasticity during in vitro cell culture over multiple cell passages, relative to a control stem cell that is not exposed to such environmental factor(s).

"Enhanced survival" as used herein may refer to a the delay, or decrease in, cell death (either apoptotic or non-apoptotic cell death) that results from exposure of stem cells to an environmental factor(s), relative to control stem cells that are not exposed to such environment factor(s).

The terms "prenatal" and "fetal" refer to the period that precedes the birth of a fetus, beginning with the formation of a diploid zygote. Thus, in the context of the invention, tissues and their associated cells derived from a fetus prior to natural birth, or birth by cesarean section, are fetal (i.e. prenatal) tissues. Tissues obtained from mammalian tissue following the birth (e.g. live and still birth) of the mammal are adult tissues and the cells derived therefrom are "adult cells."

The terms "purified" and "isolated" when used to refer to a cell population (e.g. composition of cells) means the cells in the population are essentially free from cells of a different type. A composition of cells is considered "purified," or "substantially purified," if it contains at least about 75%, at least about 80%, at least about 85%, at least about 90%, at least about 95% or at least about 100% of a desired type.

DETAILED DESCRIPTION

In some embodiments, the invention relates to the use of a combination of environmental factors and culture conditions to produce stem cells having enhanced proliferation and differentiation characteristics. In very general terms, such embodiments may be practiced by providing a population of stem cells, culturing the population of stem cells in vitro, and exposing the stem cell population to at least one environmental factor to produce a population of stem cells having enhanced differentiation and proliferation characteristics.

Environmental Factors

Aspects of the invention relate to exposing stem cells to at least one environmental factor.

Environmental factors for use with the invention include, but are not limited to, reduced oxygen tension, electromagnetic energy, mechanical energy, metabolic deprivation, barometric variation, exposure to a chemical agent, and combinations thereof.

In some embodiments of the invention, exposing stem cells to an environmental factor involves exposing the stem cells to reduced oxygen tension. In general terms, this is accomplished by contacting a composition stem cells with an environment that has a low level of ambient oxygen. The phrases "low ambient oxygen conditions," "low oxygen," and "reduced oxygen tension" refer to any oxygen concentration that is less than atmospheric oxygen. Low ambient oxygen conditions generally means any oxygen concentration below about 20%, preferably below about 15%, more preferably below about 5-10%, at sea level. Low oxygen conditions may be kept as close as possible to the normal physiological oxygen conditions in which a particular stem cell would be found in vivo. Thus, in some embodiments, the conditions employed for cells will depend on the regional origin of a particular cell; such conditions are known to the skilled artisan. "Physiologic" oxygen levels are the range of oxygen levels normally found in healthy tissues and organs.

In one embodiment, the low ambient oxygen conditions comprise an ambient oxygen condition of between about 0.25% to about 18% oxygen. In another embodiment, the ambient oxygen conditions comprise an ambient oxygen condition of between about 0.5% to about 15% oxygen. In still another embodiment, the low ambient oxygen conditions comprise an ambient oxygen condition of between about 1% to about 10% oxygen. In further embodiments, the low ambient oxygen conditions comprise an ambient oxygen condition of between about 1.5% to about 6% oxygen. Of course, these are exemplary ranges of ambient oxygen conditions to be used in culture and it should be understood that those of skill in the art will be able to employ oxygen conditions falling in any of these ranges generally or oxygen conditions between any of these ranges that mimics physiological oxygen conditions for the particular cells. Thus, one of skill in the art could set the oxygen culture conditions at 0.5%, 1%, 1.5%, 2%, 2.5%, 3%, 3.5%, 4%, 4.5%, 5%, 5.5%, 6%, 6.5%, 7%, 7.5%, 8%, 8.5%, 9%, 9.5%, 10%, 10.5%, 11%, 11.5%, 12%, 12.5%, 13%, 13.5%, 14%, 14.5%, 15%, 15.5%, 16%, 16.5%, 17%, 17.5%, 18%, 18.5%, or any other oxygen condition between any of these figures.

One aspect of the invention relates to the timing (e.g. stage of cell culture) at which the stem cells are exposed to low oxygen (i.e. reduced oxygen tension) conditions. One skilled in the art will appreciate that the timing of the exposure of the stem cells to reduced oxygen tension will depend on the stem cell characteristics that are desired. Stem cells may be exposed to reduced oxygen tension at any time during the in vitro culture of the stem cells. Stem cells may be exposed to reduced oxygen tension at times including, but not limited to, after collection of the stem cells as a tissue sample, during disaggregation of such tissue sample, during the primary culture of stem cells, during the in vitro expansion of the stem cells (e.g. over multiple cell passages), during priming (e.g. when stem cells are induced to assume a desired biological activity prior to injection into a subject), and combinations thereof.

In some embodiments of the invention, stem cells are exposed to reduced oxygen tension during the in vitro culture of the stem cells. One skilled in the art will appreciate that there are various methods for culturing stem cells under low ambient oxygen conditions (i.e. reduced oxygen tension). For example, suitable processes, reagents and equipment for practicing the invention are disclosed in the following references, which are incorporated herein by reference: U.S. Pat. No. 6,759,242; U.S. Pat. No. 6,846,641; U.S. Pat. No. 6,610,540; J. Cereb. Blood Flow Metab. 2008 Sep. 28(9):1530-42; Stem Cells. 2008 May 26(5):1325-36; Exp Neurol. 2008 April 210(2):656-70; Mol. Cell. Neurosci. (2007), doi: 10.1016/j.mcn.2007.04.003; Experimental Neurology 170, 317-325 (2001); and Neurosignals 2006-07, 15:259-265. Although these references disclose particular procedures and reagents, any low oxygen culture condition capable of expanding stem cells according to the invention may be used.

Stem cells can be exposed to low oxygen conditions under any methodology that permits the stem cells to attain an enhanced differentiation potential, proliferation rate, engraftment ability and/or in vivo migratory ability as disclosed herein. Specialized laboratory facilities may have completely enclosed environments in which the oxygen levels are controlled throughout a dedicated, isolated room. In such specialized areas, low oxygen levels can be maintained throughout the isolation, growth and differentiation of cells without interruption. Physiologic or low oxygen culturing conditions also can be maintained by using commercially-available chambers which are flushed with a pre-determined gas mixture (e.g., as available from Billups-Rothenberg, San Diego, Calif.). As an adjunct, medium can be flushed with the same gas mixture prior to cell feeding. In general, it is not possible to maintain physiologic or low oxygen conditions during cell feeding and passaging using these smaller enclosed units, and so, the time for these manipulations should be minimized as much as possible. Any sealed unit can be used for physiologic oxygen or low oxygen level culturing provided that adequate humidification, temperature, and carbon dioxide are provided.

In addition to oxygen, the other gases for culture typically are about 5% carbon dioxide and the remainder is nitrogen, but optionally may contain varying amounts of nitric oxide (starting as low as 3 ppm), carbon monoxide and other gases, both inert and biologically active. Carbon dioxide concentrations typically range around 5% as noted above, but may vary between 2-10%. Both nitric oxide and carbon monoxide are typically administered in very small amounts (i.e. in the ppm range), determined empirically or from the literature.

One aspect of the invention relates to the length of time that the stem cells are exposed to reduced oxygen tension. Under the invention, stem cells may be exposed to reduced oxygen tension for any amount of time that enhances the proliferation and differentiation of the stem cells as disclosed herein. This may be 1 or more hours, 3 or more hours, 6 or more hours, 12 or more hours, or the time may be continuous (e.g. the entire time that the stem cells are cultured in vitro). The temperature during the culture is typically reflective of core body temperature, or about 37.degree. C., but may vary between about 32 degrees centigrade and about 40 degrees centigrade.

Stem Cells and Culture Conditions

The invention may be used to expand any stem cell (or combination of stem cells) that is capable of being enhanced as disclosed herein when such stem cells, or combination of stem cells, are expanded according to the method of the invention. Suitable stem cells for use with the invention include, but are not limited to, pluripotent embryonic stem cells, mesenchymal cells, ectodermal cells, endodermal cells, and combinations thereof.

In some embodiments, the invention is practiced with ectodermal cells. Ectodermal cells for use with the invention include, but are not limited to, multipotent cells derived from the embryonic ectoderm germ layer. Suitable methods for deriving such embryonic ectodermal cells are readily available to one of ordinary skill in the art.

In some aspects of the invention, the ectodermal cells for use with the invention are neural stem cells. Neural stem cells have the ability to self-renew and differentiate to assume a plurality of different neural cell phenotypes. Neural stem cells for use with the invention may be derived from a variety of tissue compartments. In some embodiments, the neural stem cells are derived from nervous tissue. Suitable neural tissue for providing neural stem cells includes (i) the peripheral nervous system, such as for example, the nasal epithelium, pigmented epithelium, non-pigmented epithelium, and ciliary body, (ii) the spinal cord, (iii) all the regions of the brain, including but not limited to, the forebrain, basal forebrain (cholenergic neurons), cerebellum, telencephalon, mesencephalon, hippocampus, olfactory bulb, cortex (e.g., motor or somatosensory cortex), striatum, ventral mesencephalon (cells of the substantia nigra), and the locus ceruleus (neuroadrenaline cells of the central nervous system), and (iv) combinations thereof.

Instructions for deriving neural stem cells from nervous tissue, and culture conditions for expanding such neural stem cells, are readily available in the art as shown by the following publications which are incorporated herein by reference: U.S. Pat. Nos. 5,750,376, 6,497,872, and 6,777,233; U.S. Pat. Nos. 5,196,315; 5,766,948, 5,968,829; 6,468,794, 6,638,763, 6,680,198, 6,767,738, 6,852,532, 6,897,061, 7,037,719; U.S. Patent Publication Nos. 20050112109, 20040048373, 20020039789, 20020039789, 20030095956, 20050118143, 20060148083, 20050074880, 20020086422, 20040253719, 20050003531, 20050125848, 20050142569, 20060099192 and 20060134280.

Neural stem cells for expansion under the methods disclosed herein may also be derived from non-neural (e.g. non-ectodermal) tissue sources. For example, neural stem cells may be derived from mesenchymal stem cells. In some embodiments, this source of mesenchymal cells is the bone marrow. Such cells, in their undifferentiated state, assume a neural phenotype under in vitro conditions, or when introduced to the neural tissue of an animal. Amniotic fluid is another source of cells which can be differentiated into neural precursors. Instructions for deriving neural-potent bone marrow stem cells for use with the invention may be obtained from the following publications, which are incorporated by reference: U.S. Pat. Nos. 6,673,606 and 7,015,037; U.S. Patent Publication Nos. 20020164794, 20030003090, 20030039639, 20030059414, 20030203484, 20040151701, 20040208858, 20050282276, 20050249708, 20060105457, 20060177928; and Mareschi et al. Exp Hematol. 2006 November; 34(11):1563-72. In other embodiments, neural-potent mesenchymal cells are derived from umbilical cord blood. Suitable umbilical cord-derived cells, and their methods of isolation, are disclosed in U.S. Patent Publication Nos. 20020028510, 20050249708, 20040115804, 20050142118 and 20050074435, the disclosures of which are incorporated by reference. Neural-potent mesenchymal cells may also be derived from the scalp (i.e. skin) (see e.g. U.S. Patent Publication Nos. 20030003574, 20040253718 and 20040033597;

and Shih et al. Stem Cells 2005 August; 23(7) 1012-1020), the peripheral blood (see e.g. U.S. Patent Publication Nos. 20040136973 and 20050221483), the placenta (see e.g. U.S. Patent Publication Nos. 20050089513 and 20060030039) and the amniotic layer (see e.g. U.S. Patent Publication No. 20030044977).

The neural stem cells for use with the inventive method may be made using purified or non-purified cells, as well as combinations of purified and non-purified cells. Non-purified compositions of neural stem cells may be obtained in a number of ways. In some embodiments, the neural stem cell composition is made by combining separate, purified (i.e. isolated) neural stem cell populations. In other embodiments, the neural stein cell composition is obtained by culturing a mixed population of cells, such as a primary culture obtained from a tissue explant and expanded cell populations obtained therefrom. In still other embodiments, a non-purified composition of neural stem cells is obtained by combining one or more purified cell compositions, with a composition of mixed cell types such as a primary cell culture. Typically, primary cell cultures contain a mixture of cells as a variety of cells are able to grow in culture after being collected from an animal. Thus, primary cultures generally contain a combination of the different cell types which are able to proliferate in vivo. These cell types may have varying phenotypes (e.g. cellular markers) and varying levels of differentiation.

When the method is practiced using a primary culture of neural stem cells, the method generally involves the removal of a nervous tissue from an animal, disaggregation of the neural cells within the sample, and expansion of the cells in a suitable media under appropriate in vitro conditions. In general, three types of cultures can be produced, enriched either in neurons, astrocytes, or oligodendrocytes. Methods for producing primary cultures of neural stem cells are widely available in the art. One such method is disclosed in U.S. Pat. No. 5,753,491, which describes the preparation of a neural stem cell composition from fetal neural tissue. In general, this process involves the collection of fetal brain tissue from fetuses between about 7-11 weeks of gestational age. Following extraction, brain tissue is disassociated to produce a cell suspension which is subsequently plated on culture dishes and expanded under suitable conditions. Although the preparation of human fetal neural tissue is specifically called out here, one skilled in the art will appreciate that fetal neural stem cells may also be derived from both human and non-human post-natal nervous tissue. The teachings of U.S. Pat. No. 5,753,491, and all other publications referred to in this publication are incorporated by reference in their entirety.

Other methods suitable for producing a primary culture of neural cells are readily available in the art. The following publications, which are incorporated by reference, provide the teachings necessary to enable one skilled in the art to prepare a primary culture of neural stem cells for use with the invention: U.S. Pat. Nos. 5,750,376, 6,497,872 and 6,777,233; U.S. Patent Publication Nos. 20050112109, 20040048373, 20020039789, 20020039789, 20030095956, 20050118143, 20060148083, and 20050074880; Isolation, Characterization and Use of Stem Cells from the CNS, 18 Ann. Rev. Neurosci. 159-92 (1995); M. Marvin & R. McKay, Multipotential Stem Cells in the Vertebrate CNS, 3 Semin. Cell. Biol. 401-11 (1992); R. P. Skoff, The Lineages of Neuroglial Cells, 2 The Neuroscientist 335-44 (1996). A. A. Davis & S. Temple, A Self-Renewing Multipotential Stem Cell in Embryonic Rat Cerebral Cortex, 362 Nature 363-72 (1994); A. G. Gritti et al., Multipotential Stem Cells from the Adult Mouse Brain Proliferate and Self-Renew in Response to Basic Fibroblast Growth Factor, 16 J. Neurosci. 1091-1100 (1996); B. A. Reynolds et al., A Multipotent EGF-Responsive Striatal Embryonic Progenitor Cell Produces Neurons and Astrocytes, 12 J. Neurosci. 4565-74 (1992); B. A. Reynolds & S. Weiss, Clonal and Population Analyses Demonstrate that an EGF-Responsive Mammalian Embryonic CNS Precursor is a Stem Cell, 175 Developmental Biol. 1-13 (1996); Cattaneo et al., Mol. Brain. Res., 42, pp. 161-66 (1996); and B. P. Williams et al., The Generation of Neurons and Oligodendrocytes from a Common Precursor Cell, 7 Neuron 685-93 (1991).

Although fetal neural stem cell compositions are called out above, the inventive method may also be practiced with compositions derived from adult neural tissue. Such adult neural stem cells, and methods of deriving them, are taught in the following publications, the disclosures of which are incorporated by reference: U.S. Pat. Nos. 5,356,807, 5,851,832, 6,638,763 and 6,812,027; and U.S. Patent Publication Nos. 20030049234, 20030095956, 20030118566, 20040253719, 20050112109 and 20050118143.

In addition to the use of primary cultures of neural stem cells, the method of the invention further contemplates compositions of purified neural stem cells. In the context of the invention, a cell composition is "purified," or "isolated," if the cells in the composition are essentially free from cells of a different type. A composition of cells is considered "purified," " or "substantially purified," if it contains at least about 75%, at least about 80%, at least about 85%, at least about 90%, at least about 95% or at least about 100% of a desired cell type. Neural stem cells for use with the invention may be purified according to methods well known in the art, such as for example, FACS, magnetic sorting, serial passaging, cloning, and affinity chromatography. Such neural stem cells may be purified from a tissue explant or a mixed population of cells grown in culture. Suitable purified cells for practicing the invention, and the methods for making them, are disclosed in the following publications, the disclosures of which are incorporated by reference: U.S. Pat. Nos. 5,196,315, 5,766,948, 5,968,829, 6,468,794, 6,638,763, 6,680,198, 6,767,738, 6,852,532, 6,897,061 and 7,037,719; and U.S. Patent Publication Nos. 20020086422, 20040253719, 20050003531, 20050125848, 20050142569 and 20060099192.

Neural stem cells for use with the invention may also be derived from neural-potent bone marrow mesenchymal stem cells. Such cells, in their undifferentiated state, assume a neural phenotype under suitable in vitro conditions. Amniotic fluid is another source of mesenchymal stem cells which can be trans-differentiated to neural precursors for use with the invention. Instructions for deriving neural-potent bone marrow stem cells for use with the invention are provided by the following publications which are incorporated by reference: U.S. Pat. Nos. 6,673,606 and 7,015,037; U.S. Patent Publication Nos. 20020164794, 20030003090, 20030039639, 20030059414, 20030203484, 2004015.1701, 20040208858, 20050282276, 20050249708, 20060105457, 20060177928; and Mareschi et al. Exp Hematol. 2006 November; 34(11): 1563-72.

Neural-potent mesenchymal cells for use with the invention are may be derived from umbilical cord blood. Such umbilical cord-derived cells, and their methods of isolation, are disclosed in U.S. Patent Publication Nos. 20020028510, 20050249708, 20040115804, 20050142118 and 20050074435, the disclosures of which are incorporated by reference. Neural-potent mesenchymal cells may also be derived from the skin (see e.g. U.S. Patent Publication Nos. 20030003574, 20040253718 and 20040033597; and Shih et al. Stem Cells 2005 August; 23(7) 1012-1020), the peripheral blood (see e.g. U.S. Patent Publication Nos. 20040136973 and 20050221483), the placenta (see e.g. U.S. Patent Publication Nos. 20050089513 and 20060030039) and the amniotic layer (see e.g. U.S. Patent Publication No. 20030044977). The disclosures of these references are incorporated herein by reference.

Neural stem cells for use with the invention may be derived from human heterologous sources including fetal tissue following elective abortion, or from a post-natal, juvenile or adult organ donor. Autologous neural tissue can be obtained by biopsy, or from patients undergoing neurosurgery in which neural tissue is removed, for example, during epilepsy surgery, temporal lobectomies and hippocampalectomies. Neural stem cells have been isolated from a variety of adult CNS ventricular regions, including the frontal lobe, conus medullaris, thoracic spinal cord, brain stem, and hypothalamus, and proliferated in vitro using the methods detailed herein. In each of these cases, the neural stem cell exhibits self-maintenance and generates a large number of progeny which include neurons, astrocytes and oligodendrocytes.

The invention may also be used to expand a purified population of neural stem cells. Methods for providing a purified population of neural stem cells include, but are not limited to, FACS, magnetic sorting, serial passaging, cloning, and affinity chromatography. These methods may be used to purify cells from a tissue explant or a mixed population of cells grown that has been grown in culture. Suitable purified cells for practicing the invention, and the methods for making them, are disclosed in the following publications, the disclosures of which are incorporated by reference: U.S. Pat. Nos. 5,196,315, 5,766,948, 5,968,829, 6,468,794, 6,638,763, 6,680,198, 6,767,738, 6,852,532, 6,897,061 and 7,037,719; and U.S. Patent Publication Nos. 20020086422, 20040253719, 20050003531, 20050125848, 20050142569 and 20060099192.

The invention may also be practiced with mesenchymal stem cells. That is, the invention's combination of environmental factors and cell culture conditions can be used to produce a population of mesenchymal stein cells having enhanced proliferation and enhanced differentiation potential. As noted above, "enhanced," when used to refer to a stem cell's proliferation, means any measurable increase in the stem cell's mitotic cell division rate. When used to refer to a stem cell's differentiation potential, "enhanced" means retaining, or inhibiting the loss of, a stem cell's differentiation potential as the stein cell is expanded and passaged in culture.

Mesenchymal stem cells for use with the invention may be derived from any human or non-human tissue that provides stem cells capable of being expanded according to the methods disclosed herein. Suitable tissue sources include prenatal sources, postnatal sources, and combinations thereof. Tissues for deriving a suitable source of mesenchymal stem cells include, but are not limited to, bone manow, blood (peripheral blood), dermis, periosteum, synovium, peripheral blood, skin, hair root, muscle, uterine endometrium, adipose, placenta, menstrual discharge, chorionic villus, amniotic fluid and umbilical cord blood. Mesechymal stem cells may be derived from these sources individually, or the sources may be combined (before or after enrichment) to produce a mixed population of mesenchymal stem cells from different tissue sources.

Mesenchymal stem cell compositions for use with the invention may comprise purified or non-purified mesenchymal stem cells. Mesenchymal stem cells for use with the invention include those disclosed in the following references, the disclosures of which are incorporated herein by reference: U.S. Pat. No. 5,215,927; U.S. Pat. No. 5,225,353; U.S. Pat. No. 5,262,334; U.S. Pat. No. 5,240,856; U.S. Pat. No. 5,486,359; U.S. Pat. No. 5,759,793; U.S. Pat. No. 5,827,735; U.S. Pat. No. 5,811,094; U.S. Pat. No. 5,736,396; U.S. Pat. No. 5,837,539; U.S. Pat. No. 5,837,670; U.S. Pat. No. 5,827,740; U.S. Pat. No. 6,087,113; U.S. Pat. No. 6,387,367; U.S. Pat. No. 7,060,494; Jaiswal, N., et al., J. Cell Biochem. (1997) 64(2): 295 312; Cassiede P., et al., J. Bone Miner. Res. (1996) 11(9): 1264 1273; Johnstone, B., et al., (1998) 238(1): 265 272; Yoo, et al., J. Bone Joint Sure. Am. (1998) 80(12): 1745 1757; Gronthos, S., Blood (1994) 84(12): 416-44173; Basch, et al., J. Immunol. Methods (1983) 56: 269; Wysocki and Sato, Proc. Natl. Acad. Sci. (USA) (1978) 75: 2844; and Makino, S., et al., J. Clin. Invest. (1999) 103(5): 697 705.

The invention can be practiced using any culture conditions suitable for expanding a population of stein cells as disclosed herein. That is, the invention can be practiced using any cell culture conditions that, when combined with an environmental factor(s) as disclosed herein, produce a population of stem cells having enhanced proliferation, differentiation, engraftment and/or in vivo migration characteristics. As used herein, the phrase "cell culture conditions" includes, but is not limited to, medium formulations, cell culture (e.g. incubator) temperature, cell seeding density, number of passages permitted before the stem cells are harvested for use, maximum cell density (i.e. the maximum density of stem cells that is permitted before the cells are passaged), and combinations thereof. One skilled in the art will appreciate that suitable cell culture conditions will vary with the type of stem cells being cultured and the level of differentiation potential desired.

In some embodiments of the invention, stem cells are grown under conditions that incorporate the use of a culture media that comprises serum. The invention may be practiced with serum from any mammal including, but not limited to, human, bovine, goat, pig, horse, rabbit, rat, and combinations thereof. The amount of serum used may vary according to the intended use of the stem cells being cultured. In some embodiments of the invention, the stem cells are grown in media comprising less than about 5% serum. Some embodiments of the invention culture stem cells in medium containing between about 0.1% and 0.2% serum.

Utility

In some aspects, the invention is used to accelerate the manufacture of stem cells. Thus, the invention decreases the amount of time that is required to obtain a desired number of stem cells. The invention also improves the yield of stem cell manufacture by enabling the stem cells to undergo an increased number of cell passages, while retaining a desired level of differentiation potential.

In some aspects, the invention is used to modulate (i.e. increase or enhance) the therapeutic potential of the stem cell. In such embodiments, a stem cell having a first therapeutic potential is grown under suitable conditions and exposed to at least one environmental factor to produce a stem cell having a second therapeutic potential, the second therapeutic potential being greater than the first therapeutic potential. As used herein, a stem cell is considered to have greater therapeutic potential if the stem cell has an increased proliferation rate, increased in vivo migratory ability, increased differentiation potential and/or increased terminal cell activity (i.e. function), relative to a control cell that was not grown under the method of the invention. An increase in stem activity may be observed through an increase in the stem cell's in vivo migration, proliferation and/or engraftment characteristics.

In other aspects, the invention is used to enhance the in vivo migration and/or engraftment potential of a stem cell. When used in reference to "in vivo migration" or "migration," the term "enhance" means that the invention produces a measurable increase in the speed and/or distance that an implanted (e.g. transplanted) stem cell can migrate in vivo, compared to a control stem cell that has not been treated (e.g. cultured) according to the method of the invention. When used in reference to "in vivo engraftment" or "engraftmeht," the term "enhance" means that the invention produces a measurable increase in the ability of the stem cell to be accepted and nourished by the body of a subject and assume the function of the cells that are in contact with the implanted stem cell.

The invention also provides stem cells for therapeutic use. In some embodiments, the invention produces stem cells (e.g. neural stem cells) for use in a variety of central nervous system disorders. As used herein, the term "central nervous system disorder," or "CNS disorder," refers to a condition or injury that impairs the normal function of the mammalian central nervous system, such as, for example, neurodegenerative disorders, traumatic injuries (to the brain or spinal cord) and CNS dysfunctions. Neurodegenerative disorders are generally associated with a prolonged deterioration of CNS neural tissue including, but not limited to, Alzheimer's disease, Parkinson's disease, multiple sclerosis (MS), Huntington's disease, amyotrophic lateral sclerosis, cerebral palsy, Gaucher's disease, Tay-Sachs disease, Niemann Pick's disease, sphingomyelin lipidoses, and brain tumors. CNS disorders further include traumatic in juries, such as for example, hemorrhagic stroke, ischemic stroke, and mechanical injuries to the brain and spinal cord. The phrase "CNS disorder" further includes dysfunctions such as, for example, depression, epilepsy, and schizophrenia.

Although specific uses for the invention may be called out here, one skilled in the art will appreciate that the invention lends itself to any utility that benefits from the enhancement of stem cell proliferation and/or differentiation.

EXAMPLE 1

Tissue Collection and Cell Cultures

Human neural stem cells were collected from 8-10 week-old fetal brain. Brain tissue was freshly dissected and dissociated in Accutase (Sigma Aldrich) for 30 min at 37° C. The cells were seeded in different oxygen tensions and condition medium including 20% or 5% oxygen, with serum-free medium, 0.1% serum condition medium, or 0.2% serum condition medium in 100 mm cell culture dish. Neurobasal medium was used for basal medium to maintain NSCs. The components included: Neulobasal (96%; Gibco/Invitrogen, Grand Island, N.Y.); GlutaMAX (1%; Gibco/Invitrogen); Heparin (8 mg/ml; Sigma-Aldrich, St. Louis, Mo.) (26). To this added the following factors were added: basic Fibroblast Growth Factor and Epidermal growth factor (bFGF; 20 ng/ml; EGF; 20 ng/ml; human, recombinant; Chemicon International, Temecula, Calif.) with 0.1% or 0.2% FBS (Hyclone). For routine passaging, TrypLE was used as the dissociating agent (invitrogen).

Chicken Embryos

Pathogen-free fertilized chicken embryos were obtained from SPEFAS (North franklin, CT) and staged according to Hamburger and Hamilton (H&H) (1951).

Transplantation of Neural Stem Cells in Chicken Embryos.

NSCs were subcultured 72 hr prior to transplantation. Undifferentiated NSCs and differentiated NSCs were collected and a cell sample of $2 \times 10^5$ cells was prepared for each of the differentiated NSCs and undifferentiated NSCs. The cell samples were injected, i.e. transplanted into telencephalon lateral ventricle of chicken embryos at H&H stage 26. Transplanted chicken embryos were incubated at 37° C. for 6 days. Chicken embryo brains were collected and embedded with OCT Cryo Tech for cryosection.

Immunohistochemistry

Cryosection slides were placed at room temperature for 30 min. Slides were fixed by pre-cooled acetone for 5-10 min at room temperature and treated with 0.3% $H_2O_2$ in 100% methanol for 10 min to quench endogenous peroxidase activity. Slides were washed 3 times with PBS for 5 min each. Chicken brains were incubated with anti-human nestin (1:3000, chemicon international Inc.) and nuclei (1:500, Chemicon International Inc.) for one hour at room temperature. Slides were washed in PBS 3 times, 5 min for each, and exposed to secondary antibodies Alexa fluor 488-conjugated goat anti-mouse IgG (1:400) and Alexa Fluoro 647-conjugated goat anti-rabbit IgG (1:400) for 30 min at room temperature. Slides were washed with PBS 3 times, 5 min each, and counterstained with DAPI for 10 min at room temperature. Slides were washed in PBS 3 times, 5 min for each, and mounted with immunofluorescence mounting media from Sigma-Aldrich.

Results

The results showed in FIGS. 1-5 and table 1.

|  | Serum-free No. 1 | 0.1% Serum No. 2 | 0.2% Serum No. 3 | Serum-free, low oxygen No. 4 | 0.1% serum, low oxygen No. 5 | 0.2% serum, low oxygen No. 6 |
|---|---|---|---|---|---|---|
|  | $6.8 \times 10^5$ cells | $6.8 \times 10^5$ cells | $6.8 \times 10^5$ cells | $6.8 \times 10^5$ cells | $6.8 \times 10^5$ cells | $6.8 \times 10^5$ cells |
|  | 14 days | 22 days | 21 days | 9 days | 22 days | 21 days |
|  | $3.4 \times 10^5$ cells | $6.3 \times 10^6$ cells | $7.5 \times 10^6$ cells | $3.4 \times 10^5$ cells | $6.24 \times 10^6$ cells | $9.36 \times 10^6$ cells |
|  | 9 days | 11 days | 7 days | 14 days | 8 days | 7 days |
|  | $1.26 \times 10^6$ cells | $3.64 \times 10^7$ cells | $2.03 \times 10^7$ cells | $1.6 \times 10^6$ cells | $2.88 \times 10^7$ cells | $4.20 \times 10^7$ cells |
|  | 10 days | 13 days | 5 days | 10 days | 10 days | 5 days |
|  | $2.24 \times 10^6$ cells | $2.44 \times 10^7$ cells | $6.86 \times 10^6$ cells | $6.72 \times 10^6$ cells | $2.96 \times 10^7$ cells | $8.52 \times 10^6$ cells |
|  | 8 days | 14 days | 10 days | 9 days | 10 days | 6 days |
|  | $1.06 \times 10^7$ cells | $1.91 \times 10^7$ cells | $3.16 \times 10^7$ cells | $3.54 \times 10^7$ cells | $3.36 \times 10^7$ cells | $1.92 \times 10^7$ cells |
|  | 10 days |  | 10 days | 8 days | 10 days | 8 days |
|  | $3.56 \times 10^7$ cells |  | $2.47 \times 10^7$ cells | $2.94 \times 10^7$ cells | $2.38 \times 10^7$ cells | $2.06 \times 10^7$ cells |
|  | 11 days |  |  | 8 days |  | 8 days |
|  | $6.4 \times 10^6$ cells |  |  | $7.46 \times 10^6$ cells |  | $2.79 \times 10^7$ cells |
| Total | $5.26 \times 10^7$ | $7.99 \times 10^7$ | $8.35 \times 10^7$ | $7.23 \times 10^7$ | $11.58 \times 10^7$ | $11.826 \times 10^7$ |
| Passage | 6 | 4 | 5 | 6 | 5 | 6 |

We claim:

1. A method for culturing ectodermal cells comprising:
providing ectodermal cells; and
culturing said ectodermal cells under reduced oxygen tension in a medium containing serum and at least one purified growth factor;
wherein said reduced oxygen tension increases the expansion of said ectodermal cells relative to said culturing under atmospheric oxygen conditions.

2. The method of claim 1, wherein said ectodermal cells comprise neural stern cells.

3. The method of claim 1, wherein said medium comprises between about 0.02 and 2 percent serum.

4. The method of claim 1, wherein said oxygen tension is less than about 10%.

5. The method of claim 1, wherein said oxygen tension is less than about 5%.

6. The method of claim 1, wherein said at least one purified growth factor comprises epidermal growth factor, fibroblast growth factor, or a combination thereof.

7. A method for expanding ectodermal cells comprising:
providing ectodermal cells;
contacting said ectodermal cells with a medium comprising serum and at least one purified growth factor; and
culturing said ectodermal cells under low oxygen;
wherein said culturing increases the expansion of said ectodermal cells relative to said culturing under atmospheric oxygen conditions.

8. The method of claim 7, wherein said ectodermal cells are neural stem cells.

9. The method of claim 7, wherein said medium comprises less than about 5% serum.

10. The method of claim 7, wherein said medium comprises between about 0.02 and 2 percent serum.

11. The method of claim 7, wherein said low oxygen is less than about 10% oxygen.

12. The method of claim 7, wherein said low oxygen is less than about 5% oxygen.

13. The method of claim 7, wherein said at least one purified growth factor comprises epidermal growth factor, fibroblast growth factor, or a combination thereof.

* * * * *

UNITED STATES PATENT AND TRADEMARK OFFICE
CERTIFICATE OF CORRECTION

PATENT NO.         : 8,420,394 B2
APPLICATION NO.    : 12/410406
DATED              : April 16, 2013
INVENTOR(S)        : Chih-Min Lin and Alex Kharazi Page 1 of 1

It is certified that error appears in the above-identified patent and that said Letters Patent is hereby corrected as shown below:

On the Title Page, Item (76), the second inventor's name should read -- Alex Kharazi --

Signed and Sealed this
Eighteenth Day of June, 2013

Teresa Stanek Rea
*Acting Director of the United States Patent and Trademark Office*